US00H002055H

(19) United States

(12) Statutory Invention Registration (10) Reg. No.: US H2055 H

Rao et al. (43) Published: Dec. 3, 2002

(54) EXPRESSION OF TISSUE-TYPE PLASMINOGEN ACTIVATOR IN BACTERIA

(75) Inventors: Donald D. Rao, Seattle, WA (US); Margaret Y. Insley, Woodinville, WA (US)

(73) Assignee: ZymoGenetics, Inc., Seattle, WA (US)

(21) Appl. No.: 06/778,203

(22) Filed: Sep. 20, 1985

(51) Int. Cl.[7] ..... C12P 21/06

(52) U.S. Cl. ..... 435/69.2; 435/252.3; 435/252.33; 435/212; 435/320.1; 536/27; 935/9; 935/14; 935/72; 935/73

(58) Field of Search ..... 435/212, 253, 435/172.3, 320, 215; 536/27; 935/14, 29, 41, 43, 46, 73

(56) References Cited

U.S. PATENT DOCUMENTS

| | | | | |
|---|---|---|---|---|
| 4,338,397 A | | 7/1982 | Gilbert et al. | 435/68 |
| 4,411,994 A | | 10/1983 | Gilbert et al. | 435/71 |
| 4,431,740 A | | 2/1984 | Bell et al. | 435/253 |

FOREIGN PATENT DOCUMENTS

| | | | | |
|---|---|---|---|---|
| EP | 0093619 | | 11/1983 | |
| EP | 0143081 | * | 5/1985 | 435/172.3 |

OTHER PUBLICATIONS

Silhavy, T. et al, *Microbiological Reviews,* vol. 47, No. 3, p 313–314, 1983.*

Queen, C. *J. Molecular & Applied Genetics,* vol. 2, 1–10, 1983.*

Berman, P. et al, *Trends in Biotechnology,* vol. 3, No. 2, p 51–53, Feb., 1985.*

Maniatis, T. et al. Molecular Cloning, A Laboratory Manual, Colo Spring Harbor Laboratory, p 89–92, 1982.*

Kagitani, et al., *FEBS 189,* 145–149 (Sep. 1985).

Georges et al. (Gene 27: 201–211, 1984).

Pennica et al. (Nature 301: 214–221, 1983).

Edens et al. (Gene 18: 1–12, 1982).

Chan et al. (Proc. Natl. Acad. Sci. USA 78: 5401–5405 (1981).

* cited by examiner

*Primary Examiner*—Richard D. Lovering

*Assistant Examiner*—Joseph D. Anthony

(74) *Attorney, Agent, or Firm*—Seed and Berry

(57) ABSTRACT

A method, and DNA constructs useful therein, is provided for producing plasminogen activator in bacteria. Particular constructs are provided comprising a coding sequence for tissue plasminogen activator and the leader peptide thereof, which is used to transform E. coli to produce protein having activity of tissue plasminogen activator.

16 Claims, 12 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FIG.1A

```
                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                
                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                
                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                
                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                
                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                
                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                
                                                                                                                                                                                                                                                                                                                                                                                                                                                                                                                                                                                                                                                                                                                                                                                                                                                                                                                                                                                                                                                                                                                                                                                                                                                                                
```

```
                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                
```

```
                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                                
```

FIG. 1B

```
                                280                                     290                                     300
PHE ARG ILE LYS GLY GLY LEU PHE ALA ASP ILE ALA SER HIS PRO TRP GLN ALA ALA ILE PHE ALA LYS HIS ARG ARG SER PRO GLY GLU
TTT CGC ATC AAA GGA GGG CTC TTC GCC GAC ATC GCC TCC CAC CCC TGG CAG GCT GCC ATC TTT GCC AAG CAC AGG AGG TCG CCC GGA GAG
                                                        1050

                                310                                     320                                     330
ARG PHE LEU CYS GLY GLY ILE LEU ILE SER SER CYS TRP ILE LEU SER ALA ALA HIS CYS PHE GLN GLU ARG PHE PRO PRO HIS HIS LEU
CGG TTC CTG TGC GGG GGC ATA CTC ATC AGC TCC TGC TGG ATT CTC TCT GCC GCC CAC TGC TTC CAG GAG AGG TTT CCG CCC CAC CAC CTG
1100                                                                    1150

                                340                                     350                                     360
THR VAL ILE LEU GLY ARG THR TYR ARG VAL VAL PRO GLY GLU GLU GLU GLN LYS PHE GLU VAL GLU LYS TYR ILE VAL HIS LYS GLU PHE
ACG GTG ATC TTG GGC AGA ACA TAC CGG GTG GTC CCT GGC GAG GAG GAG CAG AAA TTT GAA GTC GAA AAA TAC ATT GTC CAT AAG GAA TTC
            1200                                                                    1250

                                370                                     380                                     390
ASP ASP ASP THR TYR ASP ASN ASP ILE ALA LEU LEU GLN LEU LYS SER ASP SER SER ARG CYS ALA GLN GLU SER SER VAL VAL ARG THR
GAT GAT GAC ACT TAC GAC AAT GAC ATT GCG CTG CTG CAG CTG AAA TCG GAT TCG TCC CGC TGT GCC CAG GAG AGC AGC GTG GTC CGC ACT
                            1300                                                                    1350

                                400                                     410                                     420
VAL CYS LEU PRO PRO ALA ASP LEU GLN LEU PRO ASP TRP THR GLU CYS GLU LEU SER GLY TYR GLY LYS HIS GLU ALA LEU SER PRO PHE
GTG TGC CTT CCC CCG GCG GAC CTG CAG CTG CCG GAC TGG ACG GAG TGT GAG CTC TCC GGC TAC GGC AAG CAT GAG GCC TTG TCT CCT TTC
                                        1400                                                                    1450

                                430                                     440                                     450
TYR SER GLU ARG LEU LYS GLU ALA HIS VAL ARG LEU TYR PRO SER SER ARG CYS THR SER GLN HIS LEU LEU ASN ARG THR VAL THR ASP
TAT TCG GAG CGG CTG AAG GAG GCT CAT GTC AGA CTG TAC CCA TCC AGC CGC TGC ACA TCA CAA CAT TTA CTT AAC AGA ACA GTC ACC GAC
                                                        1500

                                460                                     470                                     480
ASN MET LEU CYS ALA GLY ASP THR ARG SER GLY GLY PRO GLN ALA ASN LEU HIS ASP ALA CYS GLN GLY ASP SER GLY GLY PRO LEU VAL
AAC ATG CTG TGT GCT GGA GAC ACT CGG AGC GGC GGG CCC CAG GCA AAC TTG CAC GAC GCC TGC CAG GGC GAT TCG GGA GGC CCC CTG GTG
1550                                                                    1600

                                490                                     500                                     510
CYS LEU ASN ASP GLY ARG MET THR LEU VAL GLY ILE ILE SER TRP GLY LEU GLY CYS GLY GLN LYS ASP VAL PRO GLY VAL TYR THR LYS
TGT CTG AAC GAT GGC CGC ATG ACT TTG GTG GGC ATC ATC AGC TGG GGC CTG GGC TGT GGA CAG AAG GAT GTC CCG GGT GTG TAC ACA AAG
            1650                                                                    1700

                                520                                     527
VAL THR ASN TYR LEU ASP TRP ILE ARG ASP ASN MET ARG PRO OP
GTT ACC AAC TAC CTA GAC TGG ATT CGT GAC AAC ATG CGA CCG TGA CCAGGAACACCCGACTCCTCAAAAGCAAATGAGATCCCGCCTCTTCTTCTTCAGAAGACA
                            1750                                                                    1800

CTGCAAAGGCGCAGTGCTTCTCTACAGACTTCTCCAGACCCACCACACCGCAGAAGCGGGACGAGACCCTACAGGAGAGGGAAGAGTGCATTTTCCCAGATACTTCCCATTTTGGAAGTT
                1850                                                                    1900                                                                    1950

TTCAGGACTTGGTCTGATTTCAGGATACTCTGTCAGATGGGAAGACATGAATGCACACTAGCCTCTCCAGGAATGCCTCCTCCCTGGGCAGAAGTGGCCATGCCACCCTGTTTTCGCTAA
                                                        2000                                                                    2050

AGCCCAACCTCCTGACCTGTCACCGTGAGCAGCTTTGGAAACAGGACCACAAAAATGAAAGCATGTCTCAATAGTAAAAGAAACAAGAGATCTTTCAGGAAAGACGGATTGCATTAGAAA
                                2100                                                                    2150

TAGACAGTATATTTATAGTCACAAGGGCCCAGCAGGGCTCAAAGTTGGGGCAGGCTGGCTGGCCCGTCATGTTCCTCAAAAGCGCCCTTGACGTCAAGTCTCCTTCCCCCTTTCCCCACTC
    2200                                                                    2250                                                                    2300

CCTGGCTCTCAGAAGGTATTCCTTTTGAGTACAGTGGTGTAAAGTGTAAATCCTTTTTCTTTATAAACTTTAGAGTAGCATGAGAGAATTGTATCATTTGAACAACTAGGCTTCAGCATAT
                                                        2350                                                                    2400

TTATAGCGATCCATCGTTAGTTTTTACTTTCCGTGCCACAACCCTGTTTTATACCGTACTTAATAAATTCGGATATATTTTTTCACAGTTTTTTCCAAAAAAAAAAAAAA
```

FIG. 4A

```
                                                    190
                                                GGA GCC AGA TCT TAC CAA GTG
                                                Gly Ala Arg Ser Tyr Gln Val

        210                     225                     240                     255
ATC TGC AGA GAT GAA AAA ACG CAG ATG ATA TAC CAG CAA CAT CAG TCA TGG CTG
Ile Cys Arg Asp Glu Lys Thr Gln MET Ile Tyr Gln Gln His Gln Ser Trp Leu

                270                     285                     300
CGC CCT GTG CTC AGA AGC AAC CGG GTG GAA TAT TGC TGG TGC AAC AGT GGC AGG
Arg Pro Val Leu Arg Ser Asn Arg Val Glu Tyr Cys Trp Cys Asn Ser Gly Arg

                                                ZC88 ---->
    315                     330                     345                     360
GCA CAG TGC CAC TCA GTG CCT GTC AAA AGT TGC AGC GAG CCA AGG TGT TTC AAC
Ala Gln Cys His Ser Val Pro Val Lys Ser Cys Ser Glu Pro Arg Cys Phe Asn

            375                     390                     405
GGG GGC ACC TGC CAG CAG GCC CTG TAC TTC TCA GAT TTC GCG TGC CAG TGC CCC
Gly Gly Thr Cys Gln Gln Ala Leu Tyr Phe Ser Asp Phe Ala Cys Gln Cys Pro

420                     435                     450                     465
GAA GGA TTT GCT GGG AAG TGC TGT GAA ATA GAT ACC AGG GCC ACG TGC TAC GAG
Glu Gly Phe Ala Gly Lys Cys Cys Glu Ile Asp Thr Arg Ala Thr Cys Tyr Glu

                                        ZC89 ---->
        480                     495                     510                     525
GAC CAG GGC ATC AGC TAC AGG GGC ACG TGG AGC ACA GCG GAG AGT GGC GCC GAG
Asp Gln Gly Ile Ser Tyr Arg Gly Thr Trp Ser Thr Ala Glu Ser Gly Ala Glu

                540                     555                     570
TGC ACC AAC TGG AAC AGC AGC GCG TTG GCC CAG AAG CCC TAC AGC GGG CGG AGG
Cys Thr Asn Trp Asn Ser Ser Ala Leu Ala Gln Lys Pro Tyr Ser Gly Arg Arg

    585                     600                     615                     630
CCA GAC GCC ATC AGG CTG GGC CTG GAG AAC CAC AAC TAC TGC AGA AAC CCA GAT
Pro Asp Ala Ile Arg Leu Gly Leu Gly Asn His Asn Tyr Cys Arg Asn Pro Asp

            645                     660                     675
CGA GAC TCA AAG CCC TGG TGC TAC GTC TTT AAG GCG GGG AAG TAC AGC TCA GAG
Arg Asp Ser Lys Pro Trp Cys Tyr Val Phe Lys Ala Gly Lys Tyr Ser Ser Glu

690                     705                     720                     735
TTC TGC AGC ACC CCT GCC TGC TCT GAG GGA AAC AGT GAC TGC TAC TTT GGG AAT
Phe Cys Ser Thr Pro Ala Cys Ser Glu Gly Asn Ser Asp Cys Tyr Phe Gly Asn
```

FIG. 4B

```
        750                     765                     780                     795
GGC TCA GCC TAC CGT GGC ACG CAC AGC CTC ACC GAG TCG GGT GCC TCC TGC CTC
Gly Ser Ala Tyr Arg Gly Thr His Ser Leu Thr Glu Ser Gly Ala Ser Cys Leu

                810                     825                     840
CCG TGG AAT TCC ATG ATC CTG ATA GGC AAG GTT TAC ACA GCA CAG AAC CCC AGT
Pro Trp Asn Ser MET Ile Leu Ile Gly Lys Val Tyr Thr Ala Gln Asn Pro Ser

    855                     870                     885                     900
GCC CAG GCA CTG GGC CTG GGC AAA CAT AAT TAC TGC CGG AAT CCT GAT GGG GAT
Ala Gln Ala Leu Gly Leu Gly Lys His Asn Tyr Cys Arg Asn Pro Asp Gly Asp

            915                     930                     945
GCC AAG CCC TGG TGC CAC GTG CTG AAG AAC CGC AGG CTG ACG TGG GAG TAC TGT
Ala Lys Pro Trp Cys His Val Leu Lys Asn Arg Arg Leu Thr Trp Glu Tyr Cys

960                 975                     990                     1005
GAT GTG CCC TCC TGC TCC ACC TGC GGC CTG AGA CAG TAC AGC CAG CCT CAG TTT
Asp Val Pro Ser Cys Ser Thr Cys Gly Leu Arg Gln Tyr Ser Gln Pro Gln Phe

        1020                    1035                    1050                    1065
CGC ATC AAA GGA GGG CTC TTC GCC GAC ATC GCC TCC CAC CCC TGG CAG GCT GCC
Arg Ile Lys Gly Gly Leu Phe Ala Asp Ile Ala Ser His Pro Trp Gln Ala Ala

                1080                    1095                    1110
ATC CTT GCC AAG CAC AGG AGG TCG CCC GGA GAG CGG TTC CTG TGC GGG GGC ATA
Ile Leu Ala Lys His Arg Arg Ser Pro Gly Glu Arg Phe Leu Cys Gly Gly Ile

    1125                    1140                    1155                    1170
CTC ATC AGC TCC TGC TGG ATT CTC TCT GCC GCC CAC TGC TTC CAG GAG AGG TTT
Leu Ile Ser Ser Cys Trp Ile Leu Ser Ala Ala His Cys Phe Gln Glu Arg Phe

            1185                    1200                    1215                    1
CCG CCC CAC CAC CTG ACG GTG ATC TTG GGC AGA ACA TAC CGG GTG GTC CCT GGC
Pro Pro His His Leu Thr Val Ile Leu Gly Arg Thr Tyr Arg Val Val Pro Gly

230                 1245                    1260                    1275
GAG GAG GAG CAG AAA TTT GAA GTC GAA AAA TAC ATT GTC CAT AAG GAA TTC GAT
Glu Glu Glu Gln Lys Phe Glu Val Glu Lys Tyr Ile Val His Lys Glu Phe Asp

        1290                    1305                    1320                    1335
GAT GAC ACT TAC GAC AAT GAC ATT GCG CTG CTG CAG CTG AAA TCG GAT TCG TCC
Asp Asp Thr Tyr Asp Asn Asp Ile Ala Leu Leu Gln Leu Lys Ser Asp Ser Ser

                1350                    1365                    1380
CGC TGT GCC CAG GAG AGC AGC GTG GTC CGC ACT GTG TGC CTT CCC CCG GCG GAC
Arg Cys Ala Gln Glu Ser Ser Val Val Arg Thr Val Cys Leu Pro Pro Ala Asp
```

ZC 91

ZC 148

FIG. 4C

```
   1395                1410                1425                1440
CTG CAG CTG CCG GAC TGG ACG GAG TGT GAG CTC TCC GGC TAC GGC AAG CAT GAG
Leu Gln Leu Pro Asp Trp Thr Glu Cys Glu Leu Ser Gly Tyr Gly Lys His Glu

            1455                1470                1485                1
GCC TTG TCT CCT TTC TAT TCG GAG CGC CTG AAG GAG GCT CAT GTC AGA CTG TAC
Ala Leu Ser Pro Phe Tyr Ser Glu Arg Leu Lys Glu Ala His Val Arg Leu Tyr

500                 1515                1530                1545
CCA TCC AGC CGC TGC ACA TCA CAA CAT TTA CTT AAC AGA ACA GTC ACC GAC AAC
Pro Ser Ser Arg Cys Thr Ser Gln His Leu Leu Asn Arg Thr Val Thr Asp Asn

        1560                1575                1590                1605
ATG CTG TGT GCT GGA GAC ACT CGG AGC GGC GGG CCC CAG GCA AAC TTG CAC GAC
MET Leu Cys Ala Gly Asp Thr Arg Ser Gly Gly Pro Gln Ala Asn Leu His Asp

                1620                1635                1650
GCC TGC CAG GGC GAT TCG GGA GGC CCC CTG GTG TGT CTG AAC GAT GGC CGC ATG
Ala Cys Gln Gly Asp Ser Gly Gly Pro Leu Val Cys Leu Asn Asp Gly Arg MET

   1665                1680                1695                1710
ACT TTG GTG GGC ATC ATC AGC TGG GGC CTG GGC TGT GGA CAG AAG GAT GTC CCG
Thr Leu Val Gly Ile Ile Ser Trp Gly Leu Gly Cys Gly Gln Lys Asp Val Pro

            1725                1740                1755                1
GGT GTG TAC ACC AAG GTT ACC AAC TAC CTA GAC TGG ATT CGT GAC AAC ATG CGA
Gly Val Tyr Thr Lys Val Thr Asn Tyr Leu Asp Trp Ile Arg Asp Asn MET Arg

770             1783        1793        1803
CCG TGA CCAGGAACAC CCGACTCCTC AAAAGCAAAT GAGATCC
Pro
*                                 |←——ZC46|
```

EXPRESSION OF TISSUE-TYPE PLASMINOGEN ACTIVATOR IN BACTERIA

The present invention is directed to methods for expressing plasminogen activator in bacteria, to DNA vectors useful therein, and to protein products expressed thereby.

Blockage of blood flow in the circulatory system by the formation of blood clots is a major cause of diseases and death. The most serious problems occur when blood flow is cut off to the heart (heart attack), to the brain (stroke) or to the lungs (pulmonary embolism). To combat these problems, a group of biological compounds called the plasminogen activators functions to destroy blood clots through what is known as the fibrinolytic system. Through various mechanisms, the plasminogen activators generate the active enzyme plasmin, which in turn degrades the fibrin network of a clot to form soluble products. The two drugs which are commercially available for thrombolytic therapy which function as plasminogen activators are streptokinase, a bacterial protein, and urokinase, a serine protease isolated from human urine. Both of these drugs, however, suffer from a major drawback: they are not specific for blood clots. In addition to fibrin, they destroy such blood proteins as fibrinogen prothrombin, Factor V and Factor VIII, which may result in internal hemorrhage as a side effect of treatment. Therefore, administration of streptokinase and urokinase is usually performed by direct insertion to the site of the clot via a catheter. Since this procedure is rather intricate, it is rarely used. On the other hand, the plasminogen activators have been extracted from normal and tumor tissues and are presently classified according to the source from which they are derived: the urokinase-type plasminogen activators (uPA) and the tissue type plasminogen activators (tPA). It appears that the tPA has a higher affinity for fibrin compared to the uPA group of activators. It would thus be desirable to prepare tPA by genetic engineering techniques in order to increase the supply and variety of available tPAs.

Complementary DNA (cDNA) sequences encoding human tissue-type plasminogen activator (tPA) have been cloned and expressed in *E. coli* by Pennica, et al. (*Nature* 301: 214–221, 1983) and by Goeddel, et al. (European Patent Application Publication No. 93,619). In each of these cases, the tPA produced by the host cells was recovered through cell lysis and extraction under harsh conditions, i.e., 6M guanidine hydrochloride. The guanidine hydrochloride must subsequently be removed to permit renaturation of the protein. Goeddel, et al. show partial processing to the two-chain form of the tPA molecule, which could be inhibited by the addition of protease inhibitor.

Production of foreign proteins in bacterial cells is often hampered by difficulties in extracting the desired product from the cells. One potential solution to this problem is to direct the transformed bacterial cells to secrete the foreign protein by employing a leader peptide, but results are unpredictable. There have been attempts to produce and secrete mature foreign proteins in transformed bacterial cells using bacterial secretion signals or fused pre-sequences. Correct processing to remove the pre-sequence (bacterial or fused) has not been observed, except for limited success with some fused prepeptides. In order to obtain the desired mature foreign protein, additional (in vitro) processing is generally necessary.

It is therefore an object of the present invention to provide methods for producing mature single chain tPA in bacteria which is advantageously extracted from the cells.

It is a further object of the present invention to provide DNA vectors which are useful for expressing tPA in *E. coli*.

It is yet another object of the present invention to produce in *E. coli* a protein having the activity of human tPA.

In the accompanying FIGS.:

FIG. 4 illustrates the nucleotide sequence determined for the tPA CDNA cloned in pUCH and the amino acid sequence deduced from the nucleotide sequence. Deviations from published sequence data (Pennica et al., ibid and Wallen et al., ibid) are indicated by *. Sequences of oligonucleotides used in sequencing procedures are indicated.

Figure 5:
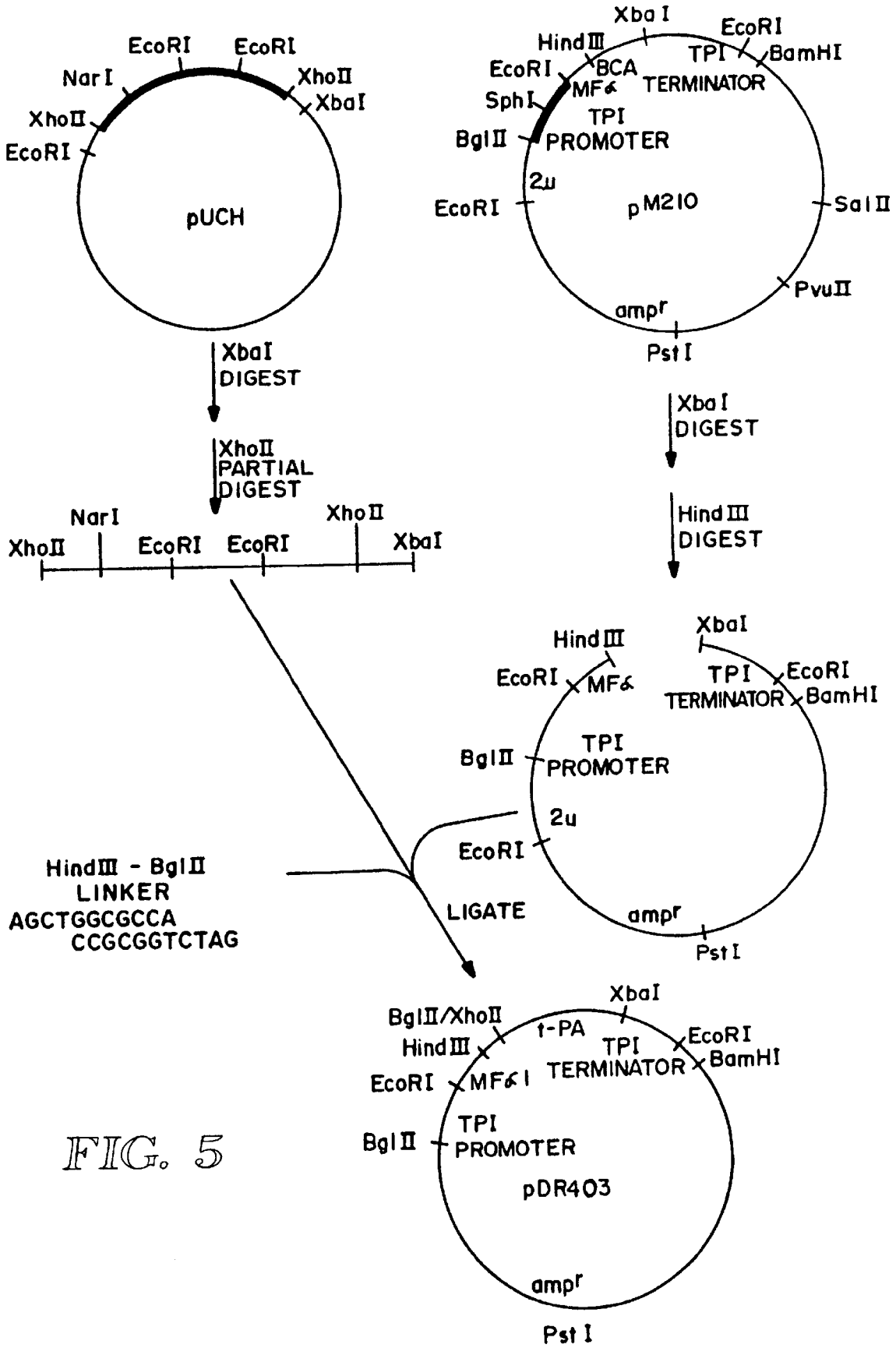

FIG. 5 illustrates the construction of the plasmid pDR403.

Figure 6:
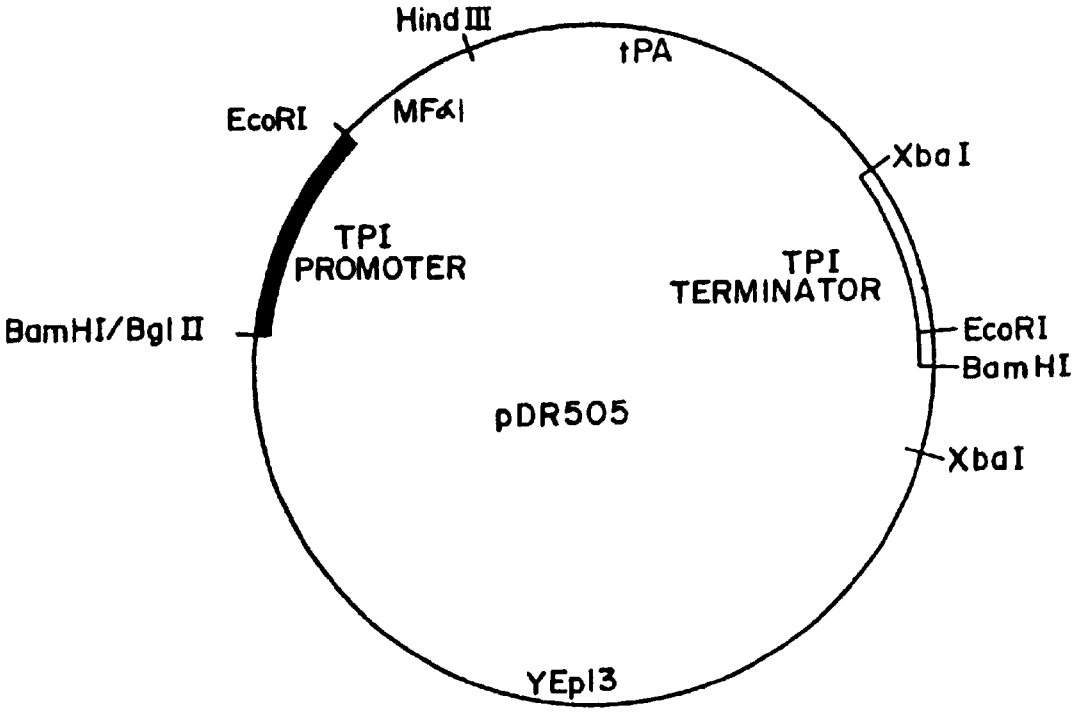

FIG. 6 illustrates the structure of the plasmid pDR505.

Figure 7:
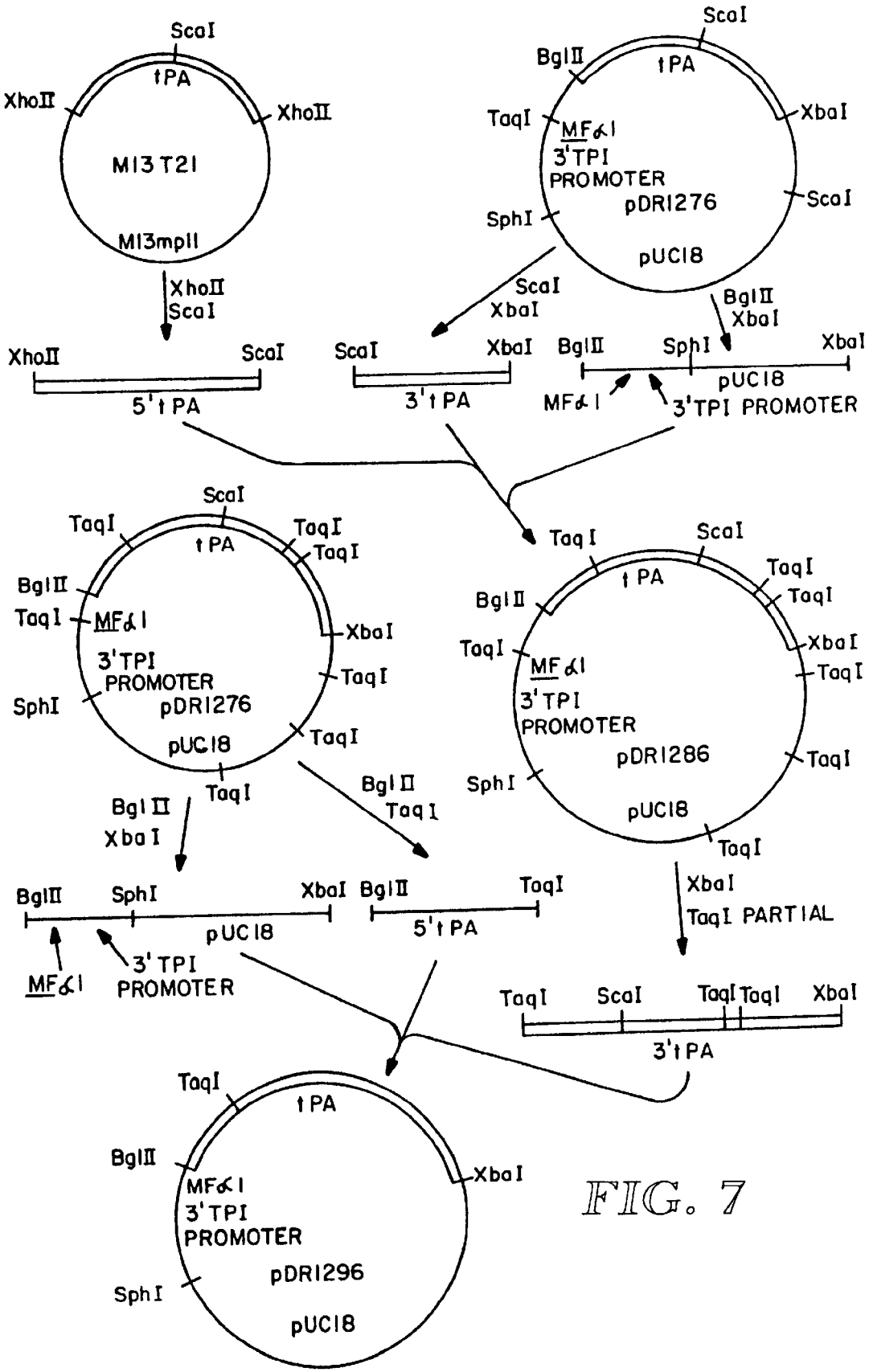

FIG. 7 illustrates the construction of the plasmid pDR1296.

Figure 8:
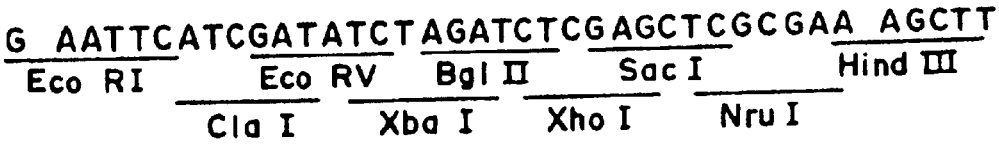

FIG. 8 illustrates a portion of the polylinker sequence in the plasmid pIC19R.

Figure 9:
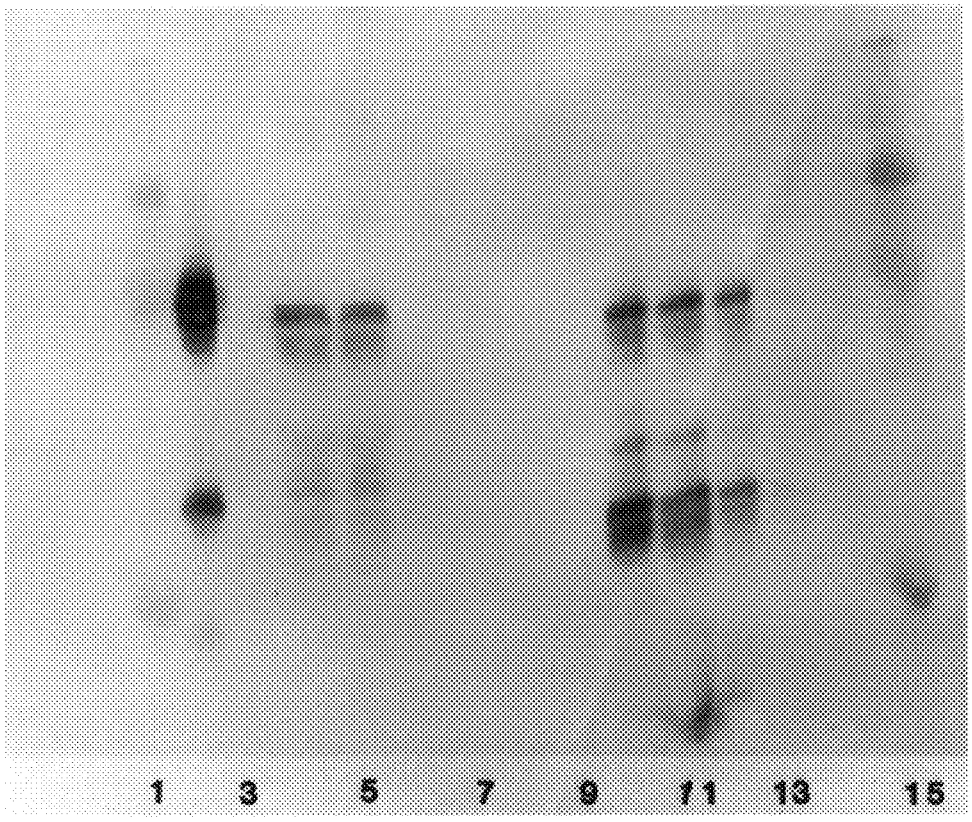

FIG. 9 shows tPA from crude extracts of *E. coli* transformed with pDR806-2 electrophoresed on a polyacrylamide gel. Lane 1, molecular size markers; lane 2, Bowes melanoma tPA; Lane 3, blank; Lane 4, *E. coli*/pDR806-2 extract.

FIG. 10 illustrates the construction of plasmid pDR806-2.

SUMMARY OF THE INVENTION

Tissue plasminogen activator is naturally produced in cells in a precursor form (prepro-tPA) comprising a leader peptide. The leader peptide, which occurs at the amino-terminus of the precursor, directs the protein into the secretion pathway of the cell and is removed from the protein during this secretion process.

The present invention is based in part on the discovery that bacterial cells, transformed with a DNA construct encoding tissue plasminogen activator and the leader peptide thereof, synthesize and process the precursor form of tPA to produce the mature single-chain form of the protein. The resultant protein product remains substantially cell associated in a form that may be removed from the ce1l-by lysis under mild conditions which do not result in denaturation of the tPA.

As used herein, the term "leader peptide" means a naturally occurring leader peptide and functional portions and derivatives thereof. The terms "leader sequence" and "signal sequence" mean the DNA sequence encoding a leader peptide.

According to the present invention, there is provided an improved method and novel DNA constructs useful therein-, of producing tPA in transformed bacterial cells wherein the tPA so produced may be advantageously extracted from the cytoplasm or periplasm of the cell. The present invention provides DNA constructs which, in a transformed bacterial cell, produce prepro tPA which is processed to mature single chain tPA which remains substantially cell-associated and may be removed from the cell by mild lysis conditions, such as by sucrose shock and treatment with lysozyme and mild detergent.

A cDNA encoding tPA may be isolated from a cDNA library made from an appropriate cell line, such as the Bowes melanoma cell line (Rijken and Collen, *J. Biol. Chem.* 256: 7035–7041, 1981), using oligonucleotide probes based on the known tPA sequence. Partial cDNA clones may be extended as necessary using synthetic oligonucleotides so that the entire coding sequence, including the leader sequence, is obtained.

For expression of tPA in a transformed bacterial cell, the coding sequence for tPA, including the leader peptide thereof, is inserted, using conventional techniques, into a suitable expression vector. The DNA encoding the leader peptide for tPA is located immediately before the structural DNA sequence for tPA and after the translational start signal (ATG) . The expression vector will usually comprise an origin of replication which is functional in bacteria and a sequence directing the initiation of t ranscription, commonly referred to as a promoter. A well known origin of replication is that of the plasmid pBR322 (Bolivar, et al., *Gene* 2: 95–113, 1977). Suitable promoters are also well known in the art, and include the bacterial lac and trp promoters, and the phage $\lambda P_R$ promoter. The $\lambda P_R$ promoter is much stronger than known bacterial promoters, and so is preferred for use in the expression of foreign genes in bacteria. Because foreign proteins may be deleterious to a transformed microorganism, or may be degraded by the microorganism, it is also preferred that a promoter be regulatable, generally through changes in the cellular environment (e.g., temperature, media composition, etc.). The $\lambda P_R$ promoter may be so regulated by incorporating the gene for the temperature sensitive repressor cI857 into the expression vector (Queen, *J. Mol. Appl. Genet.* 2: 1–10, 1983). Such an arrangement allows for growth of the host cells to a high density, at which time the expression of the cloned gene may be initiated. In this way, large amounts of foreign protein may be produced while minimizing toxicity to the host cells or degradation of the product. Other such regulatable promoters are well known in the art and include the T7 polymerase promoter (McAllister, et al., *J. Mol. Biol.* 153: 527, 1981), which is induced by the addition of phage T7 to the system; the leftward promoter ($P_L$) of phage lambda, which is thermoinducible; the tac promoter (Russel and Bennet, *Gene* 20: 231, 1982), which is derepressed by the addition of IPTG; and the trp promoter, which may be induced by the addition of IAA.

By utilizing the coding sequence for tPA including its leader peptide in a DNA construct, it has been unexpectedly found that a substantial amount of the tPA product is recoverable from the cell as mature single-chain tPA. This mature tPA remains substantially cell associated and is extractable by mild cell-lysing conditions.

The tPA produced according to the present invention may be isolated from the bacterial cells by lysing the cells using sucrose shock followed by the addition of lysozyme, EDTA and mild detergent (e.g., Triton X-100). The cell debris is then removed by centrifugation. The tPA, contained in the supernatant, may then be purified, such as by immunoadsorption using anti-tPA antibody or on a fibrincelite column.

DESCRIPTION OF THE PREFERRED EMBODIMENT

Section A below describes the construction of a preferred synthetic double stranded DNA segment which encodes the leader peptide of tPA. Section B describes the construction of preferred plasmids containing DNA sequences encoding mature tPA. Section C describes the joining of the DNA sequences encoding the tPA leader peptide and mature tPA. Section D describes the construction of plasmid pDR711. Section E describes the insertion of the tPA sequence from Section C into pDR711 to produce preferred bacterial expression vectors. Section F describes the characterization of tPA produced according to the present invention.

Standard biochemical techniques were employed throughout. Restriction endonucleases were obtained from Bethesda Research Laboratories, New England BioLabs, and Boehringer Mannheim Biochemicals, and were used according to the manufacturers' directions, generally with the addition of pancreatic RNase (10 $\mu$gml). T4 DNA ligase was obtained from Bethesda Research Laboratories and Boehringer Mannheim and was used as directed. M13 and pUC host strains and vectors (except pUC18 and pUC19) were obtained from Bethesda Research Laboratories. M13 cloning was done as described by Messing (Meth. in Enzymology 101: 20–77, 1983). DNA polymerase I (Klenow fragment) was used as described by Maniatis, et al. (*Molecular Cloning: A Laboratory Manual.* Cold Spring Harbor Labortory, 1982). *E. coli* cultures were transformed by the method of Bolivar, et al. (*Gene* 2: 95–113, 1977).

A. Preparation of a tPA Coding Fragment Comprising a Synthesized Leader Sequence.

Figure 1D:
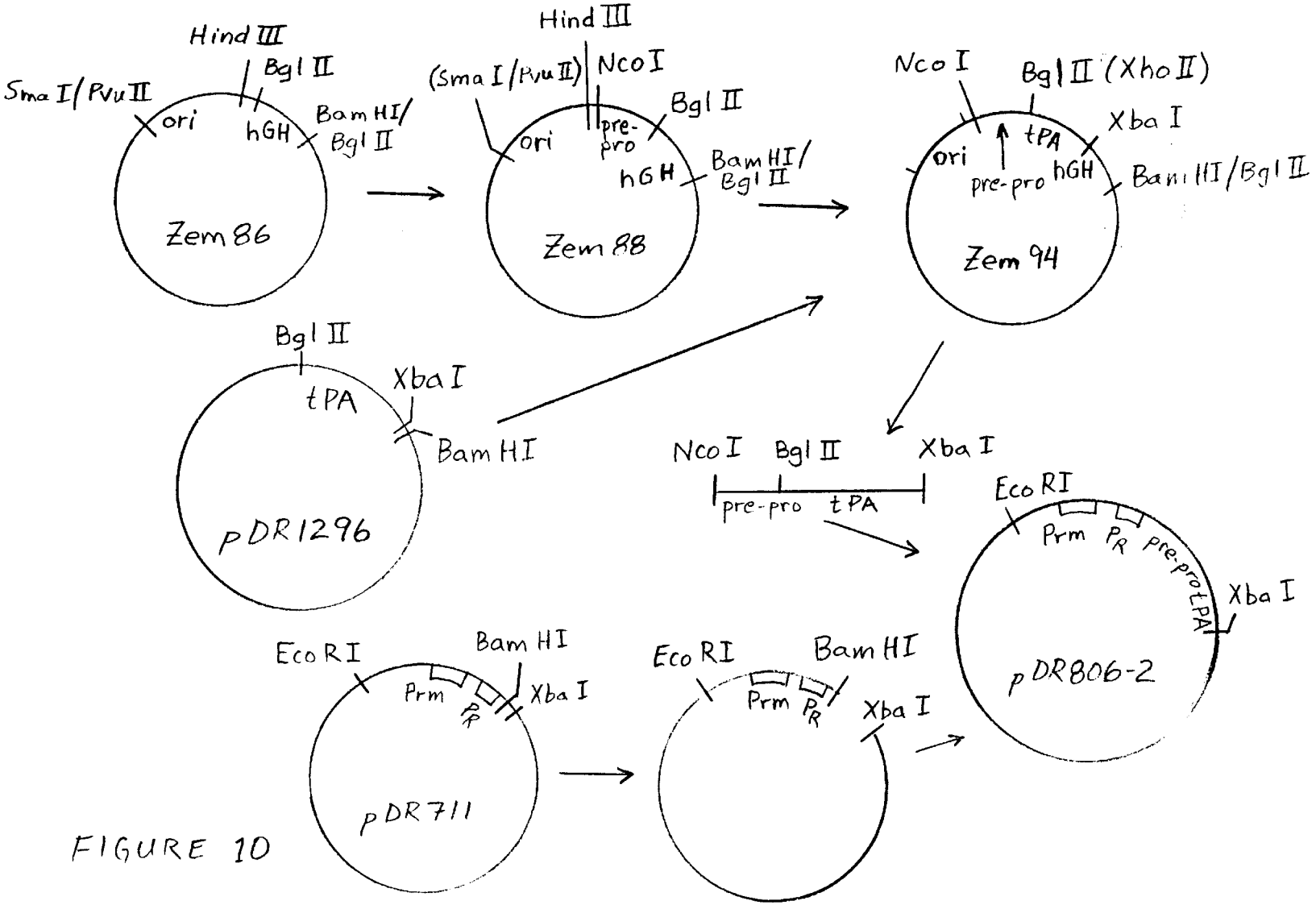
FIG. 1 illustrates the nucleotide sequence of a cDNA encoding tPA together with the deduced amino acid sequence according to Pennica et al. (*Nature* 301: 214–221, 1983).

The sequence of a human tPA cDNA clone has been reported (Pennica, et al., ibid). See FIG. 1. The sequence encoding the leader peptide comprises 115 base pairs immediately 5' to the TCT codon for amino acid number 1 (serine).

Cleavage sites for BamHI and NcoI are present immediately 5' to the first codon (ATG) of the leader sequence, and a BglII (Sau 3A, XhoII) site is located at the 5' end. The naturally occurring leader sequence lacks a convenient restriction site near the middle; however, the sequence GGAGCA (coding for amino acids −20 and −19, Gly-Ala) can be altered to GGCGCC to provide Hae III and NarI sites without changing the amino acid sequence.

The following oligonucleotides were synthesized using an Applied Biosystems Model 380-A DNA synthesizer: ZC131: $^{5'}$GGA TCC ATG GAT GCA ATG AAG AGA GGG CTC TGC TGT GTG$^{3'}$ ZC132: TGG CGC CAC ACA GCA GCA GCA CAC AGC AGAG$^{3'}$ ZC133: $^{5'}$GGC GCC GTC TTC GTT TCG CCC AGC CAG GAA ATC CATG$^{3'}$ ZC134: $^{5'}$AGA TCT GGC TCC TCT TCT GAA TCG GGC ATG GAT TTC CT$^{3'}$ Oligomers ZC131 and ZC132 were annealed to produce an overlap of 12 base pairs (Section 1). Oligomers ZC133 and ZC134 were annealed to produce an overlap of 12 base pairs (Section 2).

The oligomers were mixed in Pol I buffer (BRL), heated to 65° C. for five minutes, and slowly cooled to room temperature for four hours to anneal. Ten units of DNA polymerase I were added and the reaction proceeded for two hours at room temperature. The mixtures were electrophoresed on an 8% polyacrylamide—urea sequencing gel at 1,000 volts for 2–12 hours in order to size fractionate the reaction products. The correct size fragments (those in which the polymerase reaction went to completion) were cut from the gel and extracted.

After annealing, Section 1 was cut with BamHI and NarI and cloned into BamHI+NarI−cut pUC8. The vector pUC8 is produced as described by Vieira and Messing, Gene 19: 259–268 (1982) and Messing, *Methods in Enzymology* 101: 20–77 (19 Section 2 was reannealed and cut with NarI and BalII and cloned into BamHI+NarI−cut pUC8. Colonies were screened with appropriately labelled oligonucleotides. Plasmids identified as positive by colony hybridization were sequenced to verify that the correct sequence had been synthesized.

Section 1 was then purified from a BamHI+NarI double digest of the appropriate pUC clone. Section 2 was purified from a NarI+XhoII digest. The two fragments were joined at the NarI site and cloned into BamHI−cut pUC8.

B. Construction of a Plasminogen Activator cDNA Clone.

A cDNA library was made from the Bowes melanoma cell line (Rijken and Collen, *J. Biol. Chem.,* 256: 7035–7041, 1981) by annealing C-tailed cDNA to G-tailed pBR322 following the method of Michelson, et al. (*Proc. Natl. Acad. Sci. USA* 80: 472–476, 1983). The library was screened with oligonucleotide probes the sequences of which were determined on the basis of an amino acid sequence common to serine proteases and on the basis of the nucleotide sequence of the tPA gene as determined by Pennica et al. (ibid). The probes were synthesized by the phosphite-triester method (Beaucage and Caruthers, *Tetrahedron Letters* 22: 1859–1862, 1981; and Matteucci and Caruthers, *J. Am. Chem. Soc.* 103: 3183, 1981) using a solid support as described by Matteucci and Caruthers (*Tetrahedron Letters* 21: 719–722, 1980). Four oligonucleotide probes were used to screen this library for tPA sequences; 5' probe, $^{3'}$TAGTGAACCATTCT$^{5'}$ (sense strand, nucleotide 191 to 204); middle probe, $^{3'}$CTAGGACTATCCGT$^{5'}$ (antisense, nucleotide 810 to 823); 3' probe, $^{3'}$CTACTGTGAATGCT$^{5'}$ (antisense, nucleotide 1282 to 1295); and serine protease common probe, $^{3'}$TACGACACACGACC$^{5'}$ (antisense, nucleotide 1552 to 1565). The three partial tPA clones obtained were clone #27, containing tPA sequence from nucleotide 145 to 303; clone #20, nucleotide 749 to 1079; and clone #48, nucleotide 1156 to 1685. Nick translated tPA DNA sequences from these clones were used to screen cDNA libraries as described below to obtain two clones which together made up the complete coding sequence of mature tPA.

Figure 2:
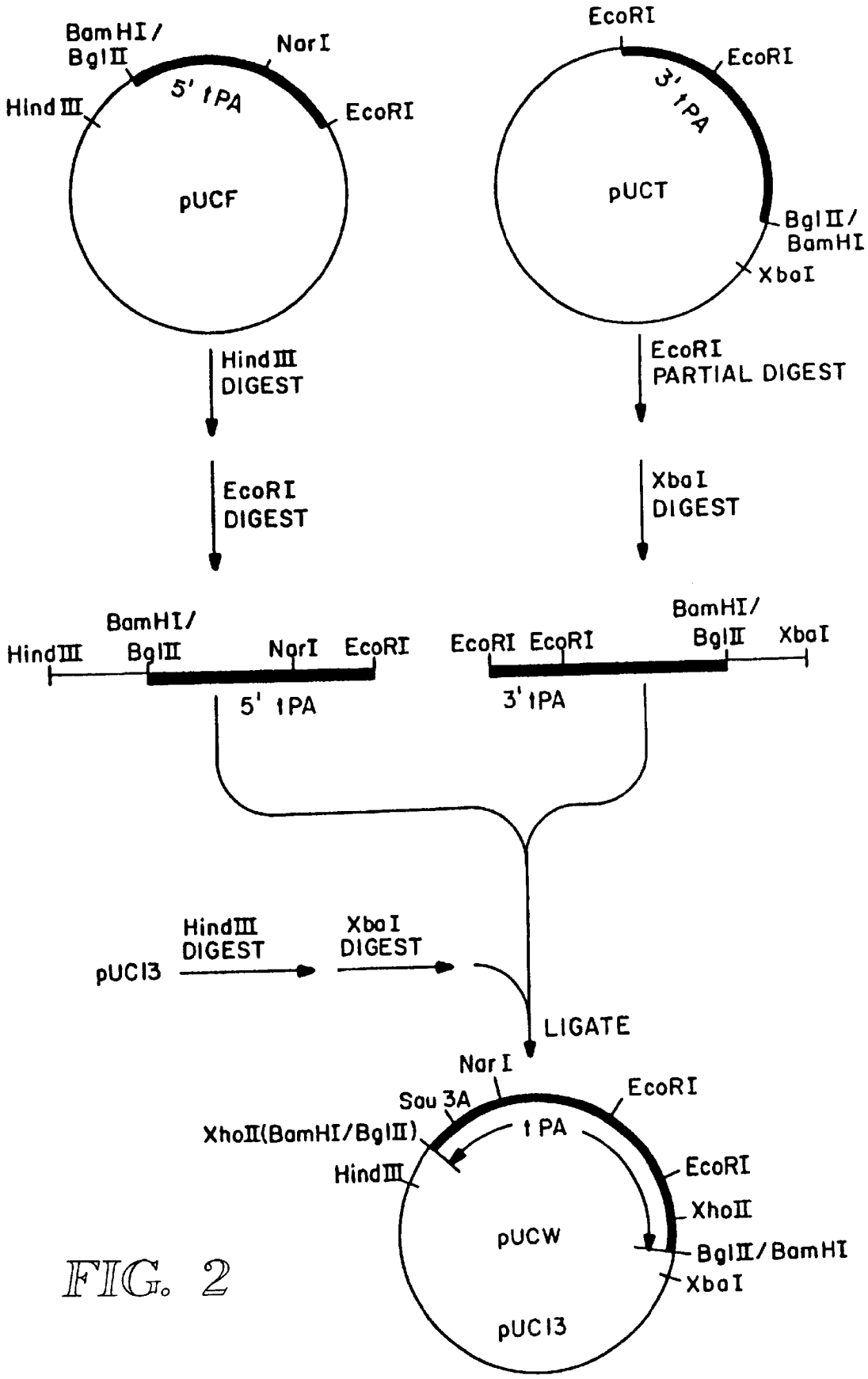
FIG. 2 illustrates the preparation of the plasmid pUCW.

Referring to FIG. 2, pUCF, containing the 5' sequence of tPA, extending from the Bgl II site at position 188 to the Eco RI site at 802, was obtained from a library constructed by double specific primer extension (Lawn et al., *Nuc. Acids Res.* 9:6103–6114, 1981), endonuclease digestion, and ligation to Bam HI, Eco RI-digested pUC13. [Vieira and Messing, *Gene* 19:259–268, 1982 and Messing, *Meth. in Enzymology* 101: 20–77, 1983]. The first strand primer was $^{3'}$CTAGGACTATCCGT$^{5'}$ which is complementary to the sequence from 810 to 823 just to the 3' side of the Eco RI site at 802. The second strand was primed using the oligonucleotide $^{5'}$AGGAAATCCATGCC$^{3'}$ which is the sequence from 155 to 168 just to the 5' side of the Bgl II site at 188. (See Pennica et al., ibid.) The library was screened using a nick translated insert of clone #27. As shown in FIG. 2, plasmid pUCF was cut with Hind III and Eco RI and the plasminogen activator-encoding fragment was purified.

Referring to FIG. 2, PUCT, containing the 3' sequence of tPA, was obtained from a library constructed as described by Michelson et al., except that after double-stranded DNA synthesis, the DNA was digested with Bgl II and Eco RI and cloned into pUC13 which had been digested with Bam HI and Eco RI. This clone was obtained by screening the library with nick translated inserts from clones #20 and #48. A partial Eco RI digest of pUCT was used to cut the plasmid at the upstream Eco RI site of the coding sequence. Subsequent digestion with Xba I resulted in an Eco RI-Xba I 3' plasminogen activator fragment, which was purified.

The two fragments, 5' tPAHind III-Eco RI and 3' tPAEco RI-Xba I, were ligated as shown in FIG. 2 into Hind III-Xba I digested pUC13 to produce plasmid pUCW.

Figure 3:
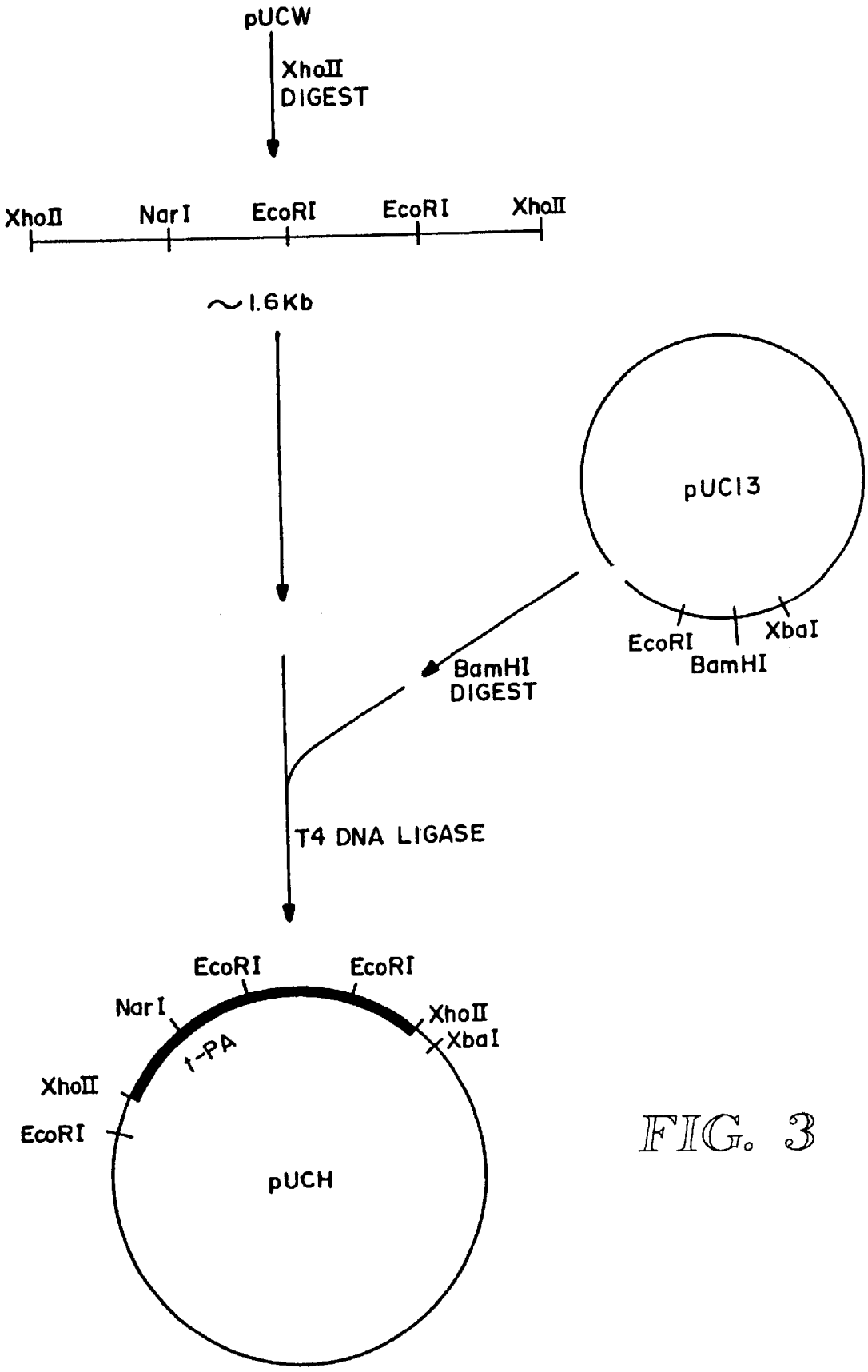
FIG. 3 illustrates the preparation of the plasmid pUCH.

To remove the 3' noncoding region of tPA from pUCW, it was digested with Xho II, which recognizes the Bam HIBgl II site at 188 and the Xho II site at 1806. This tPA Xho II fragment was cloned into the Bam HI site of pUC13. An isolate with the orientation of the tPA 3' end near the Xba I site of pUC13 was selected (FIG. 3). This construction is called pUCH.

The CDNA was sequenced to confirm that the desired sequence had been cloned. The sequencing strategy used is outlined in Table 1. Sequencing primers (except the commercial M13 universal sequencing primer from Bethesda Research Laboratories) were synthesized manually by the phosphite-triester method (Beaucage and Caruthers, *Tetrahedron Letters* 22: 1859–1862, 1981; and Matteucci and Caruthers, *J. Am. Chem. Soc.* 103: 3183, 1981) using a polymer support (Matteucci and Caruthers, *Tetrahedron Letters* 21: 719–722, 1980) or on an Applied Biosystems model 380-A DNA synthesizer. The Xho II-Xho II tPA fragment from PUCW was inserted into the Bam HI site of M13mpll (Messing, *Meth. in Enzymology* 101: 20–77, 1983) in both orientations. Fragments of this insert were subcloned into M13 vectors as indicated in Table 1. Sequencing was carried out as described by Messing (ibid). The sequence obtained is illustrated in FIG. 4.

Results indicated that the cloned sequence differed from the published (Pennica et al., ibid) sequence at four points (Table 2). The differences may have arisen in several ways, including mutation in the cell line used as a source for cDNA cloning or through copying errors made by reverse transcriptase in producing the cDNA.

To determine the correct sequence of the human tPA gene, a genomic tPA clone was obtained from a DNA library derived from normal liver tissue. The library was constructed by insertion of fetal human liver DNA fragments into bacteriophage lambda (Lawn et al., *Cell* 15: 1157–1174, 1978).

The library was used to infect *E. coli* strain LE392 (ATCC 33572) (Maniatis et al., ibid, p.504). An overnight culture of cells in L-broth containing 0.2% maltose, 10 mM $MgSO_4$, and 50 $\mu$g/ml thymidine was concentrated two-fold in 10 mM $MgSO_4$. 750 $\mu$l of the concentrate wase plated, together with 1 $\mu$l of the phage library (200,000 phage/$\mu$l) on L-broth agar in an NZY amine soft agar overlay using 22 cm×22 cm plates. Approximately $10^5$ colonies were obtained per plate following an overnight incubation at 37° C. Colonies were transferred to nitrocellulose and the lifts were treated with 0.1 M NaOH, 1.5 M NaCl for ten minutes, then neutralized in 0.2 M Tris pH 7.5, 1.5 M NaCl, air dried, and baked two hours at 80° C. Pre-hybridization and hybridization (to a full-length nick translated tPA cDNA probe) were carried out in SET buffer (SET contains, per liter, 175.2 g NaCl, 72.7 g Tris, 14.8 g EDTA, pH 8.0 with HCl) at 65° C. Filters were washed in 2xSSC, 0.1% SDS, dried, and autoradiographed. Thirteen preliminary positives were identified. Two rounds of plaque purification (screened as above) identified nine positives from the group of thirteen.

The nine positive genomic clones were plated on *E. coli* LE392, grown overnight, and lysates were prepared. The phage were purified on CsCl gradients and mapped by hybridization to oligonucleotide probes

ZC94 (5'TAGGATCCATGGATGCAATGAAGAGAGGGC3'),

ZC96 (5'CTGCTGTGTGGAGCAGTCTTCGTTTCGCCC3'),

ZC98 (5'TGCCCGATTCAGAAGAGGAGCCAGATCTTC3'),

ZC88, ZC89, ZC91, and ZC46 (see FIG. 4). Probes ZC94, ZC96, and ZC98 will hybridize to the leader peptide region, based on the published sequence (Pennica et al., ibid.); the remaining probes hybridize to the coding region. The nine positive isolates were found to fall into three distinct classes which together span the entire tPA coding region. Insert size was determined by digestion with Eco RI.

For each class, the clone having the largest insert was digested with Eco RI, Bgl II, and Eco RI+Bgl II and the restriction fragments were probed on Southern blots (Southern, *J. Mol. Biol.* 98: 503–517, 1975) using representative oligonucleotide probes. Clone number 9 was found to contain the entire coding sequence for mature tPA (but not the leader peptide coding region). Eco RI and Bgl II-Eco RI fragments of the insert from clone number 9 were inserted into M13 and pUC13 vectors for sequencing and further analysis. The fragments were sequenced by the dideoxy method (Sanger et al., *J. Mol. Biol.* 143: 161, 1983 and Sanger et al., *Proc. Natl. Acad. Sci. USA* 74: 5463, 1977) to determine the correct nucleotides at positions 404, 605, 1069, and 1725. Sequencing of a 7 kb Eco RI fragment using primer ZC89 showed that the nucleotide at position 605 in the genomic clone is guanine, in agreement with the published sequence. Sequencing of a 2.8 kb Eco RI fragment using,primer ZC148 showed that the correct nucleotide at position 1069 is thymine, in agreement with the cDNA sequence of Pennica et al (ibid). The partial amino acid sequence published by Wallen et al (ibid) provides further data indicating that the nucleotide at this position is thymine. At position 1725, the cDNA sequence showed cytosine, in contrast to the adenine found by Pennica et al. (ibid). This alteration does not affect the amino acid sequence of the protein product. The correct nucleotide at position 404 was assumed to be thymine based on the published data.

The cDNA sequence may be altered to correspond to the genomic sequence by in vitro site-specific mutagenesis (Zoller, et al., Manual for *Advanced Techniques in Molecular Cloning Course,* Cold Spring Harbor Laboratory, 1983). Sequences may be generated in which the alterations are made singly or in various combinations. The altered sequences may then be inserted into expression vectors as described below.

The plasmid pDR403 (FIG. 5), comprises the complete coding sequence of tPA (with the above-described base substitutions), including the 5' terminal sequence of the longer variant described by Wallen et al. (ibid), together with the *S. cerevisiae* TPII promoter and terminator and the pre-pro sequence from the *S. cerevisiae* MFα1 gene. This plasmid serves as a useful intermediate for the construction of other expression vectors. Plasmid pDR403, which contains the origin of replication from the bacterial plasmid pBR322, may be maintained in a suitable strain of *E. coli.* It was constructed by joining the tPA coding sequence from pUCH, together with an oligonucleotide linker, to a portion of the plasmid pM210.

Plasmid pM210 (also known as pM220) comprises the yeast TPIl promoter and terminator (Alber and Kawasaki, *J. Mol. Appl. Genet.* 1: 419–434, 1982), the MFα1 pre-pro sequence (Kurjan and Herskowitz, *Cell* 30: 933–943, 1982), and the human proinsulin (BCA) sequence (Bell et al., *Nature* 232: 525–527, 1979). *E. coli* RRl transformed with pM210 has been deposited with American Type Culture Collection under accession number 39853.

Referring to FIG. 5, to construct pDR403, plasmid pUCH was digested to completion with Xba I and partially digested with Xho II. The Xho II-Xba I tPA fragment was gel purified and joined, by means of an oligonucleotide linker, to pM210, which had been cut with Hind III and Xba I to remove the BCA sequence. The linker $^{5'}$AGCTGGCGCCA$^{3'3'}$ CCGCG-GTCTAG$^{5'}$ provides a 5' terminus complementary to the Hind III cohesive terminus of the pM210 fragment and a 3' terminus complementary to the Xho II cohesive terminus of the tPA fragment. It completes the coding sequence for the longer variant of tPA (Wallen et al., ibid) by supplying the codons for the amino acids Gly-Ala-Arg. Fusion of this sequence to the pre-pro MFαl sequence joins the tPA coding sequence in frame to the coding sequence for the Lys-Arg-Glu-Ala-Glu-Ala potential processing site of α-factor.

Subsequent sequence analysis revealed that the above-described linker sequence was present in multiple linked copies. The extraneous linker sequences were subsequently removed in the construction of vectors as described below.

The expression unit was removed from pDR403 by means of a complete Bam HI and partial Bgl II digestion. The fragment was gel purified and cloned into the Bam HI site of YEp13 (Broach et al., *Gene* 8: 121–133, 1979). The resulting plasmids were screened for the orientation of the insert. A plasmid having the orientation shown in FIG. 6 was designated pDR505.

To remove the extraneous linker sequences added in the construction of pDR403, the expression unit, comprising the 3' region of the TPIl promoter, the MFαl sequence, and the tPA coding sequence, was removed from pDR505 as a Sph I-Xba I fragment and inserted into pUC19 (Norrander et al., *Gene* 26: 101–106, 1983) which had been cleaved with Sph I and Xba I. The excess linkers were then removed by cutting with Bgl II and recircularizing the plasmid with T4 DNA ligase. The resultant construct is known as pDR1206.

The mutations in the tPA cDNA sequence were corrected by in vitro mutagenesis using essentially the two primer method of Zoller et al. (ibid). Plasmid pDR505 was cleaved with Sph I and Xba I and a 2.2 kb fragment, comprising the MFαl and tPA sequences, was purified. This fragment was joined to M13mpl9 which had been linearized with Sph I and Xba I. The resulting construct is known as mpl9-ZV52. A single (positive) strand DNA template was prepared from mpl9-ZV52. Two oligonucleotide primers were then annealed to the template. The first primer was complementary to the region around the mutagenic site except for a single base mismatch. The second primer was complementary to a sequence 40 base pairs away from the 5' terminus of the mutagenic site. Typically, the annealing reaction was run at 55° C. for ten minutes and cooled to room temperature for five minutes. DNA polymerase I (Klenow fragment) and T4 DNA ligase were then added and the primers were extended for four to eight hours at 14° C. The mixture was then used to transfect *E. coli* JM101 and the cells were plated and allowed to grow overnight. To identify positive plaques, DNA was transferred to nitrocellulose filters as described (Zoller et al., ibid), and the filters were prehybridized at 37° C. for one hour, then hybridized, at 37° C. for one hour, to the appropriate $^{32}$P-labelled mutagenic primer. Successive washes were performed at room temperature, 50° C., and, if necessary, 60° C., with autoradiography between washes. Plaques identified as positive by hybridization at the higher temperature(s) were picked and DNA was prepared therefrom. The presence of the desired sequence was verified by sequencing using the dideoxy method.

To correct the mutation at position 605, the first (mutagenic) primer was the 21-mer $^{5'}$GTTGTGGTTC-CCCAGGCCCAG$^{3'}$. The second (sequencing) primer was the 17-mer $^{5'}$CTTAAAGACGTAGCACC$^{3'}$. The positive strand of mpl9-ZV52 was used as template.

To correct the position 404 mutation, two strategies were employed. The first strategy used as template the positive strand of a phage clone carrying the corrected position 605 mutation. The second strategy used the positive strand of an uncorrected mpl9-ZV52 as template. In both cases, the mutagenic primer was the 18-mer $^{5'}$CTGGCACAC-GAAATCTGA$^{3'}$ and the sequencing primer was the 18-mer $^{5'}$GGCCCTGGTATCTATTTC$^{3'}$.

The position 1069 mutation was corrected using as template the positive strand having the position 605 mutation corrected. The mutagenic primer was the 20-mer $^{5'}$GTTGCTTGGCAAAGATGGCA$^{3'}$ and the sequencing primer was $^{5'}$GCCCCCGCACAGGAACCG$^{3'}$.

The tPA coding sequences containing one or more corrected bases were inserted into several bacterial expression vectors in the following manner. The replicative forms of the M13 clones which contained the various corrections were digested with appropriate enzymes and the tPA fragments purified. These fragments were inserted into the bacterial vector pDR1206 which was first digested with Bgl II and Xba I to remove the mutant tPA sequences. Plasmid pDR1276 was constructed from pDR1216 by insertion of the Nar I-Xba I fragment containing both the position 605 and position 1069 corrections and the Bgl II-Nar I fragment of the clone containing the position 404 correction into the linearized plasmid. This plasmid is expected to code for a tPA having the amino acid sequence as reported by Pennica et al. (ibid) and Wallen et al. (ibid).

The tPA cDNA sequence of pDR1276 was subcloned into M13mpl8 and M13mpl9 as a Sph I-Xba I fragment in order to sequence both strands. Sequencing by the dideoxy method revealed that the CDNA contained four new base substitutions at nucleotides 870, 873, 876 and 879, and a two base deletion at positions 723–724. The base substitutions at positions 404, 605 and 1069 were shown to have been corrected.

Sequencing of several subclones of intermediates in the construction of expression vectors identified which sequences could be used as sources of DNA fragments for assembly of the correct tPA sequence. M13T21, comprising the Xho II-Xho II tPA fragment of plasmid pUCW inserted into the Bam HI site of M13mpll did not contain any of the errors at positions 723–724 and 870–879, but contained the base substitutions at positions 404, 605 and 1069. Plasmid pDR1276 contained the corrected substitutions at positions 404, 605 and 1069.

Referring to FIG. 7, a vector containing the correct sequence was constructed in the following manner. The replicative form of M13T21 was digested with Xho II and Sca I and the 5' tPA fragment was purified. Plasmid pDR1276 was digested with Sca I and Xba I and the 3' tPA fragment was purified. Plasmid pDR1276 was also digested with Bgl II and Xba I and the fragment comprising the pUC18 sequences was purified. The three fragments were ligated to produce plasmid pDR1286, which contains only the original mutations at positions 404 and 605. pDR1286 was then digested completely with Xba I and partially with Taq I to obtain a 1145 base pair tPA fragment which was ligated with a 446 base pair Bgl II-Taq I fragment from pDR1276 and a Bgl II-Xba I vector fragment from pDR1276 to give the plasmid pDR1296. This plasmid thus comprises the 3' region of the TPII promoter, the MFα1 sequence, and the tPA coding sequence with all errors corrected.

TABLE 1

| SEQUENCE NAME | REGION SEQUENCED | RESTRICTION FRAGMENT | PRIMER[4] |
|---|---|---|---|
| GA20 | 190–259 | Xho II–Xho II[1] | M13 |
| Z29 | 211–378 | Xho II–Xho II[1] | TCTTACCAAGTG |
| Z88 | 362–527 | Xho II–Xho II[1] | TGCAGCGAGCCAAGG |

TABLE 1-continued

| SEQUENCE NAME | REGION SEQUENCED | RESTRICTION FRAGMENT | PRIMER[4] |
|---|---|---|---|
| Z89 | 518–687 | Xho II–Xho II[1] | ACGTGGAGCACAGCG |
| Z90 | 658–859 | Xho II–Xho II[1] | CGAGACTCAAAGCCC |
| TG48-6 | 823–990 | Eco RI–Eco RI[2] | M13 |
| Z91 | 1136–1289 | Xho II–Xho II[1] | CCCTCCTGCTCCACC |
| GS48-7REV | 1202–1018 | Eco RI–Eco RI[2] | M13 |
| Z92 | 1136–1289 | Xho II–Xho II[1] | GGGGGCATACTCATC |
| RI-HINDIII | 1279–1489 | Eco RI–Hind III[3] | M13 |
| Z93 | 1479–1648 | Xho II–Xho II[1] | TATTCGGAGCGGCTG |
| LAC | 1805–1630 | Xho II–Xho II[1] | M13 |

[1]Sequence was obtained from a construct made by inserting the tPA coding sequence from a Xho II digest of pUCW into M13mp11.
[2]The internal tPA Eco RI fragment was subcloned into Eco RI digested M13mp11.
[3]The Eco RI-Hind III fragment was subcloned into Eco RI + Hind III digested M13mp11.
[4]Primers are written 5'–3'. M13 is the universal sequencing primer for M13 obtained from Bethesda Research Laboratories.

TABLE 2

| NUCLEOTIDE | PUBLISHED SEQUENCE[1] | cDNA | AMINO ACID CHANGE |
|---|---|---|---|
| 404 | T | C | Val-Ala |
| 605 | G | A | Gly-GLu |
| 1069 | T | C | Phe-Leu |
| 1725 | A | C | None |

[1]Pennica et al, Nature 301: 214–221, 1983.

C. Joining the Synthesized Leader Sequence and cDNA

The tPA sequence of pDR1296 was joined to the synthetic signal sequence in plasmid Zem94 in the following manner. Plasmid pIC19R (comprising the polylinker sequence illustrated in FIG. 8 inserted at the Hind III site of pUC9) was digested with Sma I and Hind III. The ori region of SV40 from map position 270 (Pvu II) to position 5171 (Hind III) was then ligated to the linearized pIC19R to produce plasmid Zem67. This plasmid was then cleaved with Bgl II and the terminator region from the hGH gene (De Noto et al., *Nuc. Acids Res.* 9: 3719–3730, 1981) was inserted as a Bgl II-Bam HI fragment to produce plasmid Zem86. The synthetic tPA prepro sequence was removed from the pUC9 vector by digestion with Sau 3A. This fragment was inserted into Bgl II-digested Zem86 to produce plasmid Zem88. Plasmid pDR1296 was digested with Bgl II and Bam HI and the tPA cDNA fragment was isolated and inserted into Bgl II-cut Zem88. The resultant plasmid was designated Zem94. Plasmid Zem94 was digested with Nco I and the resultant ends blunted using Si nuclease. The linearized plasmid was then digested with Xba I and the ca. 1766 base pair tPA fragment was purified.

D. Construction of pDR711

Plasmid pCQV2 (Queen, *J. Mol. Appl. Genet.* 2: 1–10, 1983) was digested with Eco RI and Bam HI and the ca. 900 bp fragment comprising the $\delta P_R$ and Prm promoters was separated on a 1% low-melting agarose gel. The 900 base pair band was cut from the gel, incubated at 45° C. for 5 minutes in TE buffer (10 mM Tris pH 7.4, 5 mM EDTA), extracted with phenol-choloroform, and ETOH precipitated. This fragment was then inserted into pUC12 (Vieira and Messing, Gene 19: 259–268, 1982; and Messing, *Meth. in Enzymology* 101: 20–77, 1983) which had been cut with Eco RI and Bam HI to produce pDR711.

E. Construction of pDR806-2 Expression Vector and Expression of tPA Therefrom.

Referring to FIG. 10, Plasmid pDR806-2 was constructed as follows. To construct an expression vector for producing tPA in an *E. coli* transformant, plasmid pDR711 was first cut with Bam HI and the resultant ends blunted using S1 nuclease. The linearized plasmid was then cut with Xba I, and the ca. 3.9 kb fragment was purified by electrophoresis on low-melting agarose and extraction in TE buffer. This vector fragment was joined to the 1766 bp fragment from plasmid Zem94. The ligation mixture was used to transform *E. coli* LM1035 (a high transforming derivative of strain HB101 [ATCC 33694]). Twenty-five transformants were selected and screened for expression of tPA essentially by the method of Helfman et al. (*Proc. Nat'l. Acad. Sci. USA* 80: 31–35, 1983) using rabbit anti-tPA polyclonal antiserum and goat anti-rabbit IgG coupled to horseradish peroxidase. Two positive transformants were identified.

The two transformants were further screened by restriction enzyme digestion. Bgl II +Eco RI double digests produced fragments of 3532, 1000, 614 and 472 base pairs, as expected for the correct construction. Xba I+Eco RI double digests produced the expected fragments of 3000, 1614, 532 and 472 base pairs. One such plasmid was designated pDR806-2. It was sequenced and shown to contain the complete coding sequence for pre-pro tPA. *E. coli* LM1035 transformed with pDR806-2 has been deposited with American Type Culture Collection under accession number 53227.

*E. coli LM*1035 transformed with pDR806-2 were grown in L-broth+ampicillin at 32° C. to early exponential phase. The temperature was then raised to 42° C. Aliquots were taken for assay at 30 minutes, 6.0 minutes and 90 minutes after the temperature shift, and after overnight incubation.

Culture samples (25 ml) were centrifuged and the pellets washed once with $H_2$ O. The pellets were resuspended in 900 $\mu$l of 20% sucrose in 100 mM. Tris pH 8.0. The cells were lysed by addition of 100 $\mu$l of 5 mgml lysozyme in 50 mM EDTA with incubation for 10 minutes at room temperature. The spheroplasts were pelleted and the periplasmic supernatant fraction removed for subsequent assay. The spheroplasts were resuspended in 100 $\mu$l of sucroseTris buffer, 850 $\mu$l of lysis buffer (0.3% Triton X-100, 150 mM Tris pH 8.0, 0.2 M EDTA) were added and the mixture placed on ice for 30 minutes. The resultant lysates were centrifuged one hour at 35,000 RPM in a Beckman SW 50 rotor. The supernatants (cytoplasm+membrane fraction) were removed and assayed for biological activity (by the fibrin lysis method) and for tPA polypeptide (by ELISA). Results were compared to purified tPA standards. Assay results (Table 3) indicate that the specific activity of the product is highest shortly after the temperature shift and decreases with time.

The fibrin lysis assay is based on the method of Binder et al. (*J. Biol. Chem.* 254: 1998, 1979). 10 ml of a bovine fibrinogen solution (3.0 mg/ml in 0.036 M sodium acetate pH 8.4, 0.036 M sodium barbital, 0.145 M NaCl, 104 M $CaCl_2$, 0.02% $NaN_3$) were added to 10 ml of a 1.5% solution of low melting temperature agarose in the same buffer at 40° C. To this solution were added 10 $\mu$l of bovine thrombin (500 U/ml). The mixture was poured onto a Gelbond agarose support sheet (Marine Colloids) and allowed to cool. Wells were cut in the agarose and to the wells were added 10 $\mu$l of the sample to be tested plus 10 $\mu$l of phosphate buffered saline containing 0.1% bovine serum albumin. Results were compared to a standard curve prepared using purified tPA. The development of a clear halo around the well indicates the presence of biologically active plasminogen activator. Results are given in Table 3.

For the enzyme-linked immunosorbent assay (ELISA), microtiter plate (Immulon 2, Dynatech) wells were coated with affinity purified rabbit anti-tPA antibody using 200 $\mu$l of a 1:400 dilution of antibody in 0.1 M $Na_2CO_3$ pH 9.6. The plates were allowed to stand at 4° C. overnight, then were washed three times with buffer B (0.05% Tween 20, 0.05% $NaN_3$, in phosphate buffered saline). 200 $\mu$l of buffer A (0.05% Tween 20, 0.05% $NaN_3$, 1% BSA in phosphate buffered saline) were added to each well and the plates were incubated for 2 hours at 37° C. to reduce nonspecific binding. Plates were then washed three times with buffer B.

Test samples were prepared by diluting the material to be tested in buffer A. 200 $\mu$l of sample were added per well and the plates were incubated one hour at room temperature. Wells were aspirated and washed three times with buffer B and once with distilled water. 200 $\mu$l of a solution of affinity purified rabbit anti-tPA antibody coupled to alkaline phosphatase in buffer A (typically a 1:800 dilution of conjugated antibody) were added to each well and the plates were incubated 30 minutes at room temperature. The antibody solution was then removed and the plates washed as above with buffer B and distilled water. 200 $\mu$l of enzyme substrate (60 mg para-nitrophenyl phosphate reagent (Sigma) in 50 ml of a solution of 96 ml/l diethanolamine, 56 mg/l $MgCl_2$, pH 9.8) were added and the plates incubated at 37° C. for 30 minutes. Plates were read on a Titertek "Multiskan" detector. Results are shown in Table 3.

TABLE 3

| Time After | Fibrin Lysis, $\mu$g/l | | ELISA, $\mu$g/l Cytoplasm + |
|---|---|---|---|
| 42° C. Shift | Periplasm | Cytoplasm + Membrane | Membrane |
| 30 min | 0.375 | 12.5 | 12.5 |
| 60 min | 1.60 | 12.5 | 30.0 |
| 90 min | 3.0 | 14.5 | 50.0 |
| Overnight (>14 Hr) | 0.325 | 0.275 | <12.5 |

Expression levels obtained from pDR806-2 were compared to expression from a comparable plasmid which lacked the tPA leader sequence. This plasmid, pDR805, comprises the lambda CI857 represser gene and PR promoter, and a tPA coding sequence with a 5' initiator ATG, inserted into pUC12.

Plasmid pDR805 was tested for tPA expression as described for pDR806-2. tPA polypeptide was detected (by ELISA) at levels as high as 125 u$\mu$g/l. However, no fibrin lysis activity was observed.

F. Characterization of tPA Produced in *E. Coli*

The tPA protein made by *E. coli* LM1035 transformed with pDR806-2 was characterized by analysis on Western blots, essentially as described by Towbin et al. (*Proc. Natl. Acad. Sci. USA* 76: 4350, 1979). A PBS/0.2% Triton X-100 extract was electrophoresed, transferred to nitrocellulose, and probed with a rabbit polyclonal antibody to tPA, followed by goat anti-rabbit antibody conjugated to horseradish peroxidase. The tPA was visualized using 4-chloro-1-napthol HRP Color Development Reagent (BioRad). As shown in FIG. 9, most of the immunologically reactive material migrated slightly faster than the single chain Bowes Melanoma tPA standard, indicating a lack of glycosylation in the bacterial product.

We claim:

1. A DNA construct, capable of directing the production of human tissue plasminogen activator in a transformed bacterial cell, comprising a coding sequence for human pre-pro tissue plasminogen activator; and a promoter positioned such that expression of said coding sequence in said cell is directed by said promoter.

2. A DNA construct according to claim 1 wherein the human tissue plasminogen activator produced by said cell remains substantially associated with the cytoplasm and cell membrane.

3. A DNA construct according to claim 2 wherein said human tissue plasminogen activator is removable from said cell following lysis under mild lysis conditions.

4. A DNA construct according to claim 1 wherein said human tissue plasminogen activator produced by said cell is substantially in the form of a single chain polypeptide having a molecular weight in the range of 58,000 to 65,000 daltons.

5. A DNA construct according to claim 4 wherein said promoter is regulated by modulating the environment of the cell.

6. A DNA construct according to claim 5 wherein said promoter is regulated by a change in temperature.

7. A transformed bacterial cell containing a DNA construct according to any of claims 1 through 6.

8. A transformed bacterial cell according to claim 7 wherein the cell is *E. coli.*

9. A transformed bacterial cell according to claim 8 wherein the *E. coli* is ATCC Deposit No. 53227.

10. A DNA construct according to claim 1 wherein the DNA construct is pDR806-2.

11. A method for producing human tissue plasminogen activator in a bacterial cell comprising the steps of:

a. transforming said cell with a DNA construct comprising a coding sequence for human pre-pro tissue plasminogen activator, and a promoter positioned in said construct such that the expression of said coding sequence in said cell is directed by said promoter; and b. extracting said human tissue plasminogen activator from said cell.

12. The method of claim 11 wherein said extraction of said human tissue plasminogen activator produced by said cell comprises:

lysing said cell by mild osmotic shock and treatment with lysozyme to produce spheroplasts;

lysing the spheroplasts; and recoving human tissue plasminogen activator from the lysed spheroplasts.

13. The method of claim 11 wherein said human tissue plasminogen activator expressed by said cell is substantially in the form of a single-chain polypeptide having a molecular weight in the range of 58,000 to 65,000 daltons.

14. The method of claim 11 wherein said promoter is regulated by modulating the environment of the cell.

15. The method of claim 14 wherein said promoter is regulated by a change in temperature.

16. The method of claim 11 wherein said cell is *E. coli.*

* * * * *